(12) United States Patent
Weiguo et al.

(10) Patent No.: US 8,530,704 B2
(45) Date of Patent: Sep. 10, 2013

(54) METHOD OF PRODUCING FLUOROMETHYL 1,1,1,3,3,3-HEXAFLUOROISOPROPYL ETHER

(75) Inventors: Xu Weiguo, Hangzhou (CN); Hua Li, Hangzhou (CN)

(73) Assignee: Zhejiang Lantian Environmental Protection Hi-tech Co., Ltd., Hangzhou, Zhejiang Province (CN)

( * ) Notice: Subject to any disclaimer, the term of this patent is extended or adjusted under 35 U.S.C. 154(b) by 225 days.

(21) Appl. No.: 13/123,190

(22) PCT Filed: Aug. 25, 2009

(86) PCT No.: PCT/CN2009/073484
§ 371 (c)(1),
(2), (4) Date: Apr. 7, 2011

(87) PCT Pub. No.: WO2010/022645
PCT Pub. Date: Mar. 4, 2010

(65) Prior Publication Data
US 2011/0257440 A1    Oct. 20, 2011

(30) Foreign Application Priority Data
Aug. 27, 2008   (CN) .......................... 2008 1 0120621

(51) Int. Cl.
*C07C 43/00*   (2006.01)
(52) U.S. Cl.
USPC .......................................................... 568/683

(58) Field of Classification Search
None
See application file for complete search history.

(56) References Cited

U.S. PATENT DOCUMENTS

| | | | |
|---|---|---|---|
| 3,683,092 A | 8/1972 | Regan et al. | |
| 3,689,571 A | 9/1972 | Regan et al. | |
| 3,897,502 A | 7/1975 | Russell et al. | |
| 3,911,024 A | 10/1975 | Croix | |
| 4,250,334 A | 2/1981 | Coon et al. | |
| 4,469,898 A | 9/1984 | Coon et al. | |
| 6,303,831 B1 * | 10/2001 | Bieniarz et al. | 568/604 |
| 6,469,219 B1 | 10/2002 | Khrimian et al. | |
| 2004/0073070 A1 | 4/2004 | Sharratt et al. | |
| 2006/0205825 A1 * | 9/2006 | Terrell et al. | 514/722 |

FOREIGN PATENT DOCUMENTS
CN  1431987 A  7/2003
WO  WO9725303  7/1997

* cited by examiner

*Primary Examiner* — Sudhakar Katakam
(74) *Attorney, Agent, or Firm* — Jacobson Holman PLLC; Jiwen Chen

(57) ABSTRACT

The present invention provides a preparation method of fluoromethyl 1,1,1,3,3,3-hexafluoroisopropyl ether by reacting $CH_2FX$ with 1,1,1,3,3,3-hexafluoroisopropanol in the presence of acid-binding agent. The reaction can be also preformed in the presence of solvent and/or phase-transfer catalyst. The present method has the advantages of simple reaction, manageable control condition, high material conversion and product yield, and the product can be easily separated. The obtained fluoromethyl 1,1,1,3,3,3-hexafluoroisoprophyl ether can be used as a safe inhalation anesthetics.

24 Claims, No Drawings

METHOD OF PRODUCING FLUOROMETHYL 1,1,1,3,3,3-HEXAFLUOROISOPROPYL ETHER

This is a U.S. national stage application under 35 U.S.C. 371 of PCT/CN2009/073484, filed on Apr. 25, 2009 and published in Chinese, claiming priority from Chinese Application No. 200810120621.8, filed Aug. 27, 2008, which is hereby incorporated by reference.

FIELD OF THE INVENTION

The invention relates to a preparation method of fluoromethyl 1,1,1,3,3,3-hexafluoroisopropyl ether, particularly to reacting of $CH_2FX$ with 1,1,1,3,3,3-hexafluoroisopropanol in the presence of acid-binding agent.

BACKGROUND OF THE INVENTION

Fluoromethyl 1,1,1,3,3,3-hexafluoroisopropyl ether (also named as sevoflurane) is a widely applied inhalation anesthetics, which shows advantages of low blood & air partition coefficient, nonirritant, free of inflammability and explosion, stable and quick anesthesia induction, easy operation, revivification within short period, manageable controlled anesthetic depth, etc., thus presenting wide application in operation anesthesia.

There are 6 major preparation methods of fluoromethyl 1,1,1,3,3,3-hexafluoroisopropyl ether, ie. with reaction of $CX_2F_2$ (X is halogen) with 1,1,1,3,3,3-hexafluoroisopropanol, 1,1,1,3,3,3-hexafluoroisopropanol with formaldehyde (trioxymethylene) and non-aqueous hydrogen fluoride in the presence of concentrated sulfuric acid as dehydrant, 1,1,1,3,3,3-hexafluoroisopropanol with $CH_2FOCH_2F$, $(CF_3)_2CHOCH_2CL$ with fluorinating reagents, and bromine trifluoride with $(CN)_2CHOCH_3$, etc.

U.S. Pat. No. 6,303,831 discloses a method of preparing halomethyl hexafluoroisopropyl ether by reacting 1,1,1,3,3,3-hexafluoroisopropanol with $CX_2F_2$ (X is halogen) in the presence of alkality, followed by sevoflurane in the presence of fluorinating reagents following fluorination. Reaction for 18 h will help convert 1,1,1,3,3,3-hexafluoroisopropanol up to 92% and yield sevoflurane up to 40%. The major disadvantages of such preparation method are long reaction time, reaction in two steps, low rate of feedstock conversion (less selection of product), low yield, high price of feedstock $CB_{r2}F_2$ and $Cl_2F_2$, etc.

U.S. Pat. No. 3,683,092, U.S. Pat. No. 3,689,571 and U.S. Pat. No. 3,911,024 disclose a method of preparing sevoflurane by reacting chloromethyl 1,1,1,3,3,3-hexafluoroisopropyl ether with potassium fluoride, sodium fluoride, hydrogen fluoride or bromine trifluoride following halogen exchange. In the presence of potassium fluoride and sodium fluoride acting as fluorinating reagents, high-boiling point solvent, like sulfolane, is required to aid reaction at high temperature up to 250-325° C. and high pressure up to 60-80 atmos. Such reaction may last a long period with low yield. In the presence of non-aqueous hydrogen fluoride acting as fluorinating reagent, reaction may occur at temperature of 50-80° C. and at atmospheric pressure, giving low rate of conversion for feedstock and 50-60% of yield. In the presence of bromine trifluoride acting as fluorinating reagent, reaction may easily take place. However, bromine trifluoride is pretty expensive. The above 3 patents also disclose a method of producing methyl-2,2,2-trifluoro-(trifluoromethane) ethyl ether first by reacting 1,1,1,3,3,3-hexafluoroisopropanol with dimethyl sulfate and sodium hydroxide solution, and then chloromethyl-1,1,1,3,3,3-hexafluoroisopropyl ether by chloridizing methyl-2,2,2-trifluoro-(trifluoromethane) ethyl ether with chlorine. It is a complex reaction.

WO97/25303 and US2004/00730070 provide a method of preparing methyl chloride 1,1,1,3,3,3-hexafluoroisopropyl ether, plus unreacted twin (methyl chloride) ether and acetal, by mixing twin (methyl chloride) ether ($CH_2FOCH_2F$), 1,1,1,3,3,3-hexafluoroisopropanol with sulfuric acid. The reaction requires $CH_2FOCH_2F$ as feedstock not easily available and gives low yield as low as 30% (measured as 1,1,1,3,3,3-hexafluoroisopropanol).

U.S. Pat. No. 4,250,334, U.S. Pat. No. 4,469,898 and U.S. Pat. No. 6,469,219 provide a method of producing sevoflurane with fluoromethylation process, ie. add concentrated sulfuric acid and hydrogen fluoride into paraformal-dehyde to obtain a reaction mixture, and then pipette 1,1,1,3,3,3-hexafluoroisopropanol into the mixture under the heating condition to obtain the gas to be collected. The method, however, may generate dimenthoxym ethane, acetal and other byproducts, plus unavoidable fluoro-ether products other than methyl fluoride-1,1,1,3,3,3-hexafluoroisopropyl ether, with 1,1,1,3,3,3-hexafluoroisopropanol conversion rate of only 33-38%. Meanwhile, the target product—fluoromethyl 1,1,1,3,3,3-hexafluoroisopropyl ether partially forms fluoromethyl 1,1,3,3,3-pentafluoroisopropenyl ether following decomposition reaction. Such two products are not easily separated due to close boiling point. Furthermore, the process requires a large amount of concentrated sulfuric acid as dehydrant and hydrogen chloride as fluorating agent. Hydrogen chloride is so corrosive that equipment and pipelines impose high requirement on its material. Reaction will give rise to a large amount of inorganic or organic acid waste water, thus bringing about many serious problems on treatment of three wastes (waste gas; waste water; industrial residue) for the commercial production.

U.S. Pat. No. 3,897,502 provides a method of producing fluoromethyl 1,1,1,3,3,3-hexafluoroisopropyl ether by subjecting methyl-2,2,2-trifluoro-1-(trifluoromethane) ethyl ether to 20% fluoride diluted with argon with fluoridation. The method gives low yield, and used fluoride is highly toxic and expensive, which is not easily controlled in applications.

Therefore, it is necessary to develop a new preparation method of fluoromethyl 1,1,1,3,3,3-hexafluoroisopropyl ether to address the above concerns.

SUMMARY OF THE INVENTION

To address concerns in the above processes, such as long reaction time, complex reaction procedure, limited selection of product, low yield, difficult post-treatment, high requirements on reaction conditions, expensive raw materials, etc., the inventor develops a new preparation method of fluoromethyl 1,1,1,3,3,3-hexafluoroisopropyl ether. The present method is characterized by simple reaction, manageable control condition, high material conversion and product yield, and easy separation of the product.

For the purpose, the inventor adopts measures below:

A preparation method of fluoromethyl 1,1,1,3,3,3-hexafluoroisopropyl ether is characterized by allowing reaction of compounds as listed in General form (1) with 1,1,1,3,3,3-hexafluoroisopropanol in the presence of acid-binding agent.

$$CH_2FX \quad (1)$$

Wherein: X is either Cl, Br or I.
since $CH_2FCL$, $CH_2FBr$ and $CH_2FI$ show increased reaction activity in turn, reaction with 1,1,1,3,3,3-hexafluoroisopropanol provides outcomes of progressive increase in turn under the same conditions. $CH_2FI$ is, however, expensive so that priority is given to $CH_2FI$ and next $CH_2FBr$ in terms of operability and economy.

The acid-binding agent as stated in the invention relates to a kind of alkaline substance added in the reaction process to absorb acid generated in the reaction. The acid-binding agent may react with acid to form salt, thus preventing reaction or reaction balance from acid impact.

The acid-binding agent is a kind of inorganic base or organic base or such combination. The inorganic base is a kind of metal oxide, metal hydroxide, metal carbonate or metal acid carbonate or such combination. Metal oxide is a kind of alkali metal oxide or alkali soil metal oxide or such combination. Metal hydroxide is a kind of alkali metal hydroxide or alkali soil metal hydroxide or such combination. Metal carbonate is a kind of alkali metal carbonate or alkali soil metal carbonate or such combination. Metal acid carbonate is a kind of alkali metal acid carbonate or alkali soil metal acid carbonate or such combination.

In terms of availability and price, etc., alkali metal hydroxide gives priority to sodium hydroxide or potassium hydroxide. The above inorganic bases may be added into the reactor either in the form of water solution or solid.

Organic base is a kind of pyridine or amine or such combination. The amine may be triethylamine, diethylamine, monoethanolamine, diethanol amine, 1,2-propylene diamine, tert-butylamine.

The invention may occur in the presence of solvent, or at the absence of solvent. Reaction with solvent is the first option. The solvent may be water, straight chain ether, cyclic ether, nitrile compound, N,N-dimethyl formamide, N,N-dimethyl acetamide, N-methylpyridine flavanone or dimethyl sulfoxide or such combination. Straight chain ether gives priority to ether and/or dimethoxyethane. Cyclic ether gives priority to dioxane and/or tetrahydrofuran. Nitrile compound gives priority to acetonitrile and/or propionitrile.

One of above solvents or such combination may be added into the reaction process. The invention specifies no limited usage of solvent. In consideration of economy and commercial availability, mass ratio of solvent to 1,1,1,3,3,3-hexafluoroisopropanol is preferably 50:1~1:1, and further optimized to 7:1~1:1.

The invention may be also performed in the presence of phase-transfer catalyst. The phase-transfer catalyst may be quaternary ammonium salt, phosphonium salt, oxidized sulfonium salt, pyridine salt or polyether compound or such combination. Quaternary ammonium salt may be tetrabutyl ammonium bromide, tetraethyl ammonium bromide or tetrabutyl ammonium hydrogen sulfate. Phosphonium salt gives priority to triphenylphosphine. Polyether compound gives priority to polyethylene glycol.

The invention specifies no limited usage of phase-transfer catalyst. In terms of economy and reaction outcome, mol ratio of phase-transfer catalyst to 1,1,1,3,3,3-hexafluoroisopropanol is preferably 0.0001:1~1:1, and further optimized to 0.01:1~0.2:1.

The invention imposes no particular requirements on reaction temperature. Reaction may be accelerated at high temperature. On the other hand, reaction at extremely high temperature will reduce selectivity of reaction, generating a large amount of olefin and olefin polymer. Reaction temperature is preferably controlled at 0-300° C., ideally at 0-100° C.

The invention may take place under pressurized condition or normal atmosphere in a continuous or intermittent way. Continuous feeding is the first option. No special requirements on reaction pressure are specified. In terms of accelerated reaction, reaction may be promoted at high pressure. However, reaction at overpressure condition may give rise to formation of hydrogen fluoride, thus forming byproduct—fluoromethyl 1,1,3,3,3-pentafluoroisopropenyl ether. Also, generated olefin is prone to polyreaction to viscous polymer with large molecular weight, thus leading to reduced selectivity of reaction product. As a result, reaction pressure gives priority to 0.1-2.0 MPa, or even 0.1-0.5 MPa, or eventually 0.1-0.3 MPa.

The invention specifies no limited usage of acid-binding agent. In terms of accelerated reaction and reduced cost of raw material, mol ratio of 1,1,1,3,3,3-hexafluoroisopropanol to acid-binding agent is preferably 2:1~1:2. Over-usage of acid-binding agent may lead to formation of byproduct $(CF_3)_2CHOCH_2X$, and cause reaction product—sevoflurane to be disintegrated into fluoromethyl 1,1,3,3,3-pentafluoroisopropenyl ether, thus affecting product yield and requiring more separation processes.

In theory, the invention may be fulfilled with any feeding ratio of $CH_2FX$ to 1,1,1,3,3,3-hexafluoroisopropanol. Increased portion of $CH_2FX$ in feed will favor accelerated reaction and conversion rate of 1,1,1,3,3,3-hexafluoroisopropanol. In the event of extremely high portion of $CH_2FX$ in feed, $CH_2FX$ may be partially lost unavoidably in spite of recycling use of $CH_2FX$, and more recycling treatment processes are required, thus leading to higher cost of product. Therefore, mol ratio of $CH_2FX$ to 1,1,1,3,3,3-hexafluoroisopropanol is preferably 20:1~0.5:1, ideally 3:1~0.8:1.

The reactor for the invention may be glass flask, or stainless steel-based or tetrafluoride-lined HP kettle. The selection of the reactor is governed by the reaction pressure.

Another preparation method of fluoromethyl 1,1,1,3,3,3-hexafluoroisopropyl ether for the invention is to subject $CH_2FBr$ to reaction with 1,1,1,3,3,3-hexafluoroisopropanol in the presence of acid-binding agent, solvent and phase-transfer catalyst.

The acid-binding agent may be one of above inorganic bases or organic bases or such combination, with priority being given to sodium hydroxide and/or potassium hydroxide. The phase-transfer catalyst may be one of above compounds, ie. quaternary ammonium salt, phosphonium salt, oxidized sulfonium salt, pyridine salt or polyether compound or such combination. Quaternary ammonium salt may be tetrabutyl ammonium bromide, tetraethyl ammonium bromide or tetrabutyl ammonium hydrogen sulfate. Phosphonium salt gives priority to triphenylphosphine. Polyether compound gives priority to polyethylene glycol. The solvent may be water, straight chain ether, cyclic ether, nitrile compound, N,N-dimethyl formamide, N,N-dimethyl acetamide, N-methylpyridine flavanone or dimethyl sulfoxide or such combination. Straight chain ether gives priority to ether and/or dimethoxyethane. Cyclic ether gives priority to dioxane and/or tetrahydrofuran. Nitrile compound gives priority to acetonitrile and/or propionitrile.

Mass ratio of solvent to 1,1,1,3,3,3-hexafluoroisopropanol is preferably 50:1~1:1, and further optimized to 7:1~1:1. Mol ratio of 1,1,1,3,3,3-hexafluoroisopropanol to acid-binding agent is preferably 2:1~1:2, ideally 0.01:1~0.2:1. Mol ratio of phase-transfer catalyst to 1,1,1,3,3,3-hexafluoroisopropanol is preferably 0.0001:1~1:1, and further optimized to 0.01:1~0.2:1. Reaction temperature is preferably controlled at 0-300° C. ideally at 0-100° C. Reaction pressure gives priority to 0.1-2.0 MPa, or further 0.1-0.5 MPa, or ideally 0.1-0.3 MPa.

The products and unreacted materials for the invention may be separated with any methods available in the field, such as separating method, rectifying method, column chromatography, etc., with priority being given to the separating method and rectifying method. At the end of reaction, separate the products out of the reaction process with separating or rectifying method for further separation and purification, which is easily progressed.

Reacted products are subject to qualitative analysis with mass spectrum and quantitative analysis with gas chromatography.

The invention may occur with water as solvent. The acid-binding agent and phase-transfer catalyst may be utilized in the form of water solution. With water as solvent, the reacted product is sevoflurane nearly insoluble in water. The post-reaction solution is split into two layers. Separation of lower organic layer will provide sevoflurane. Thus, post-processing is easily controlled. 1,1,1,3,3,3-hexafluoroisopropanol is soluble in water. With the post-reaction status still under weak base condition, quick separation of 1,1,1,3,3,3-hexafluoroisopropanol with organic phase is expected. As per the invention, the reaction with water as solvent will be appropriately controlled by using the phase-transfer catalyst so as to give satisfied results.

The invented preparation method of fluoromethyl 1,1,1,3,3,3-hexafluoroisopropyl ether has the advantages of simple reaction, manageable control condition, high material conversion and product yield, and the product can be easily separated. Therefore, it is an ideal process for commercial application.

DESCRIPTION OF THE PREFERRED EMBODIMENT

Detailed description of the present invention is given below for illustration and not intended to limit this invention.

Embodiment 1

Added in a three-neck flask of 250 ml are 90 g of 1,1,1,3,3,3-hexafluoroisopropanol, 71 g of fluoroiodomethane and 31 g of potassium hydroxide. Reaction may take place for 10 h at temperature of not more than 40° C. and agitation speed of 300 r/min. Allow the solution after reaction for distillation to obtain 80 g of colorless transparent solution. Analysis on distilled solution with gas chromatography shows fluoroiodomethane conversion rate of 95%, and 85.05% of sevoflurane in 80 g of solution. The reaction has a yield of 80.65% with fluoroiodomethane standard. Unreacted 1,1,1,3,3,3-hexafluoroisopropanol and fluoroiodomethane can be recovered for reuse.

Embodiment 2

Added in a tetrafluoride-lined HP kettle of 500 ml are 30 g of 1,1,1,3,3,3-hexafluoroisopropanol, 10 g of sodium hydroxide and 150 g of DMF at one time before closing the kettle. The kettle, when purged with nitrogen, is filled with 36 g of fluorochloromethane. Warm up the HP kettle to 90° C., and allow the reaction for 6 h at agitation speed of 300 r/min. Allow the solution after reaction for distillation to obtain 20 g of colorless transparent solution. Analysis on distilled solution with gas chromatography shows 1,1,1,3,3,3-hexafluoroisopropanol conversion rate of 96%, and 80% of sevoflurane in 20 g of solution. The reaction has a yield of 46.69% with 1,1,1,3,3,3-hexafluoroisopropanol standard. Unreacted 1,1,1,3,3,3-hexafluoroisopropanol and fluorochloromethane can be recovered for reuse.

Embodiment 3

Change the way of feeding fluorochloromethane to continuous feeding, with other conditions kept the same as those for Embodiment 2. Carry out distillation at the end of reaction to obtain 25 g of pale yellow transparent solution. Analysis on such solution with gas chromatography shows 1,1,1,3,3,3-hexafluoroisopropanol conversion rate of 98%, and 75% of sevoflurane in 25 g of solution. The reaction has a yield of 53.44% with 1,1,1,3,3,3-hexafluoroisopropanol standard. Unreacted 1,1,1,3,3,3-hexafluoroisopropanol and fluorochloromethane can be recovered for reuse.

Embodiment 4

Adopt a 500 ml stainless steel kettle as reactor, with other conditions kept the same as those for Embodiment 2. The solution after reaction is split into two layers. Separated pale yellow organic layer at the lower part weighs 32 g. Analysis on such pale yellow solution with gas chromatography shows 1,1,1,3,3,3-hexafluoroisopropanol conversion rate of 95%, and 70% of sevoflurane in the solution. The reaction has a yield of 65.86% with 1,1,1,3,3,3-hexafluoroisopropanol standard. Unreacted 1,1,1,3,3,3-hexafluoroisopropanol and fluorochloromethane can be recovered for reuse.

|  | Sevoflurane, g | Selectivity, % | Conversion rate, % | Yield, % |
| --- | --- | --- | --- | --- |
| Embodiment 2 | 16.00 | 80 | 96 | 46.69 |
| Embodiment 3 | 18.75 | 75 | 98 | 53.44 |
| Embodiment 4 | 22.40 | 70 | 98 | 65.86 |

According to the above embodiments, it is evident that continuous feeding is beneficial for improvement of conversion rate and yield of target product. Also, stainless steel kettle performs better than tetrafluoride-lined one.

Embodiment 5

Added in a three-neck flask of 250 ml are 30 g of 1,1,1,3,3,3-hexafluoroisopropanol, 100 g of N-methylpyrrolidone, 20 g of bromofluoromethane and 2 g of polyethylene glycol-600. Put 20 g of sodium carbonate in water to prepare sodium carbonate solution, to be slowly pipetted into the reaction process to control exothermal rate and prevent surging reaction temperature. Enable the reaction for 8 h at agitation speed of 300 r/min and room temperature. Allow the solution after reaction for distillation to obtain 32 g of colorless transparent solution. Analysis on distilled solution with gas chromatography shows 1,1,1,3,3,3-hexafluoroisopropanol conversion rate of 88%, and 78.24% of sevoflurane in 32 g of solution. The reaction has a yield of 79.51% with 1,1,1,3,3,3-hexafluoroisopropanol standard. Unreacted 1,1,1,3,3,3-hexafluoroisopropanol and bromofluoromethane can be recovered for reuse.

Embodiment 6

Added in a stainless steel kettle of 500 ml are 50 g of 1,1,1,3,3,3-hexafluoroisopropanol, 60 g of N-methylpyrrolidone and 21 g of fluorochloromethane. Put 45 g of sodium carbonate in water at reaction temperature of not more than 50° C. to prepare sodium carbonate solution, to be slowly pipetted into the reaction process. Enable the reaction for 6 h at agitation speed of 300 r/min and reaction temperature of 50° C. Allow the solution after reaction for distillation to obtain 45 g of pale yellow transparent solution. Analysis on distilled solution with gas chromatography shows fluorochloromethane conversion rate of 80%, and 78.02% of sevoflurane in 45 g of solution. The reaction has a yield of 71.57% with fluorochloromethane standard. Unreacted 1,1,1,3,3,3-hexafluoroisopropanol and fluorochloromethane can be recovered for reuse.

Embodiment 7

Added in a three-neck flask of 250 ml are 30 g of 1,1,1,3,3,3-hexafluoroisopropanol, 100 g of water, 1 g of polyethylene glycol-400 and 30 g of fluoroiodomethane. Put 10 g of potassium hydroxide in 40 g of water to prepare potassium hydroxide solution, to be slowly pipetted into the reaction process to control exothermal rate and prevent surging reaction temperature. Enable the reaction for 10 h at appropriate agitation speed and room temperature. There are two layers in the solution after reaction. Separated colorless transparent organic layer at the lower part weighs 38 g. Analysis on separated solution with gas chromatography shows 1,1,1,3,3,3-hexafluoroisopropanol conversion rate of 100%, and 80.11% of sevoflurane in the solution of 38 g. The reaction has a yield of 85.03% with 1,1,1,3,3,3-hexafluoroisopropanol standard. Unreacted fluoroiodomethane can be recovered for reuse.

|  | Sevoflurane, g | Selectivity, % | Conversion rate, % | Yield, % |
| --- | --- | --- | --- | --- |
| Embodiment 5 | 25.04 | 78.24 | 88 | 79.51 |
| Embodiment 6 | 35.11 | 78.02 | 80 | 71.57 |
| Embodiment 7 | 30.44 | 80.11 | Approx. 100 | 85.03 |

According to the above embodiments, it is evident that addition of phase-transfer catalyst is beneficial for improvement of conversion rate, selectivity and yield of target product. Also, reaction at high temperature may speed up the reaction and enhance conversion rate.

Embodiment 8

Added in a tetrafluoride-lined kettle of 500 ml are 50 g of 1,1,1,3,3,3-hexafluoroisopropanol, 60 g of N-methylpyrrolidone, 4 g of tetrabutyl ammonium hydrogen sulfate, 21 g of fluorochloromethane, 54 g of potassium carbonate and 150 g of water. Enable the reaction for 9 h at agitation speed of 300 r/min and room temperature. Allow the solution after reaction for distillation to obtain 48 g of colorless transparent solution. Analysis on distilled solution with gas chromatography shows fluorochloromethane conversion rate of 86%, and 77.65% of sevoflurane in 48 g of solution. The reaction has a yield of 70.70% with fluorochloromethane standard. Unreacted 1,1,1,3,3,3-hexafluoroisopropanol and fluorochloromethane can be recovered for reuse.

Embodiment 9

Make replacement of 21 g fluorochloromethane with 35 g bromofluoromethane, with other conditions kept the same as those for Embodiment 8 to permit reaction for 9 h. Allow the solution after reaction for distillation to obtain 50 g of colorless transparent solution. Analysis on distilled solution with gas chromatography shows bromofluoromethane conversion rate of 84%, and 80.53% of sevoflurane in 50 g of solution. The reaction has a yield of 78.20% with bromofluoromethane standard. Unreacted 1,1,1,3,3,3-hexafluoroisopropanol and bromofluoromethane can be recovered for reuse.

Embodiment 10

Make replacement of fluorochloromethane with 49 g fluoroiodomethane, with other conditions kept the same as those for Embodiment 8 to permit reaction for 9 h. Allow the solution after reaction for distillation to obtain 59 g of colorless transparent solution. Analysis on distilled solution with gas chromatography shows fluoroiodomethane conversion rate of 100%, and 91.23% of sevoflurane in 59 g of solution. The reaction has a yield of 87.81% with fluoroiodomethane standard. Unreacted 1,1,1,3,3,3-hexafluoroisopropanol can be recovered for reuse.

|  | Sevoflurane, g | Selectivity, % | Conversion rate, % | Yield, % |
| --- | --- | --- | --- | --- |
| Embodiment 8 | 37.27 | 77.65 | 86 | 70.70 |
| Embodiment 9 | 40.27 | 80.53 | 84 | 78.20 |
| Embodiment 10 | 53.83 | 91.23 | 100 | 87.81 |

Embodiment 11

Added in a three-neck flask of 250 ml are 30 g of 1,1,1,3,3,3-hexafluoroisopropanol, 100 g of N,N-dimethyl formamide, 20 g of bromofluoromethane and 5 g of tetrabutyle ammonium bromide. Put 20 g of potassium hydroxide in 40 g of water to prepare sodium hydroxide solution, to be slowly pipetted into the reaction process. Enable the reaction for 6 h at agitation speed of 300 r/min and room temperature. Allow the solution after reaction for distillation to obtain 30 g of colorless transparent solution. Analysis on distilled solution with gas chromatography shows bromofluoromethane conversion rate of 80%, and 75.43% of sevoflurane in 30 g of solution. The reaction has a yield of 79.90% with bromofluoromethane standard. Unreacted 1,1,1,3,3,3-hexafluoroisopropanol and bromofluoromethane can be recovered for reuse.

Embodiment 12

Make replacement of bromofluoromethane with 12 g fluorochloromethane, with other conditions kept the same as those for Embodiment 11 to permit reaction for 6 h. Allow the solution after reaction for distillation to obtain 25 g of colorless transparent solution. Analysis on distilled solution with gas chromatography shows fluorochloromethane conversion rate of 73%, and 72.15% of sevoflurane in 25 g of solution. The reaction has a yield of 69.80% with fluorochloromethane standard. Unreacted 1,1,1,3,3,3-hexafluoroisopropanol can be recovered for reuse.

Embodiment 13

Make replacement of bromofluoromethane with 28 g fluoroiodomethane, with other conditions kept the same as those for Embodiment 11 to permit reaction for 6 h. Allow the solution after reaction for distillation to obtain 34 g of colorless transparent solution. Analysis on distilled solution with gas chromatography shows fluoroiodomethane conversion rate of 94%, and 88.03% of sevoflurane in 34 g of solution. The reaction has a yield of 89.91% with fluoroiodomethane standard. Unreacted fluoroiodomethane and 1,1,1,3,3,3-hexafluoroisopropanol can be recovered for reuse.

|  | Sevoflurane, g | Selectivity, % | Conversion rate, % | Yield, % |
| --- | --- | --- | --- | --- |
| Embodiment 11 | 22.63 | 75.43 | 80 | 79.90 |
| Embodiment 12 | 18.04 | 72.15 | 73 | 69.80 |
| Embodiment 13 | 29.03 | 88.03 | 94 | 89.91 |

Embodiment 14

Added in a stainless steel HP kettle of 500 ml are 30 g of 1,1,1,3,3,3-hexafluoroisopropanol, 15 g of triethylamine and 150 g of acetonitrile at one time before closing the kettle. The kettle, when purged with nitrogen, is filled with 10 g of fluorochloromethane. Warm up the HP kettle to 60° C., and allow the reaction for 8 h at agitation speed of 300 r/min. Allow the solution after reaction for distillation to obtain 21 g of pale yellow transparent solution. Analysis on distilled solution with gas chromatography shows fluorochloromethane conversion rate of 76%, and 71.73% of sevoflurane in 21 g of solution. The reaction has a yield of 67.88% with fluorochloromethane standard. Unreacted 1,1,1,3,3,3-hexafluoroisopropanol and fluorochloromethane can be recovered for reuse.

Embodiment 15

Make replacement of fluorochloromethane with 17 g bromofluoromethane, with other conditions kept the same as those for Embodiment 14 to permit reaction for 8 h. Allow the solution after reaction for distillation to obtain 28 g of colorless transparent solution. Analysis on distilled solution with gas chromatography shows bromofluoromethane conversion rate of 89%, and 78.01% of sevoflurane in 28 g of solution. The reaction has a yield of 81.80% with bromofluoromethane standard. Unreacted bromofluoromethane and 1,1,1,3,3,3-hexafluoroisopropanol can be recovered for reuse.

Embodiment 16

Make replacement of fluorochloromethane with 27 g fluoroiodomethane, with other conditions kept the same as those for Embodiment 14 to permit reaction for 8 h. Allow the solution after reaction for distillation to obtain 30 g of colorless transparent solution. Analysis on distilled solution with gas chromatography shows fluoroiodomethane conversion rate of 99%, and 90.52% of sevoflurane in 30 g of solution. The reaction has a yield of 91.43% with fluoroiodomethane standard. Unreacted fluoroiodomethane and 1,1,1,3,3,3-hexafluoroisopropanol can be recovered for reuse.

|  | Sevoflurane, g | Selectivity, % | Conversion rate, % | Yield, % |
|---|---|---|---|---|
| Embodiment 14 | 15.06 | 71.73 | 76 | 67.88 |
| Embodiment 15 | 21.84 | 78.01 | 89 | 81.80 |
| Embodiment 16 | 27.08 | 90.52 | 99 | 91.43 |

According to the above embodiments, reaction of $CH_2FI$ with 1,1,1,3,3,3-hexafluoroisopropanol performs best to give the highest conversion rate, selectivity and yield of target product under the same conditions. $CH_2FBr$ ranks next. Similarly, improved ratio of $CH_2FX$ to 1,1,1,3,3,3-hexafluoroisopropanol is beneficial for the reaction, leading to improvement of conversion rate, selectivity and yield of target product.

Embodiment 17

Added in a stainless steel kettle of 500 ml are 30 g of 1,1,1,3,3,3-hexafluoroisopropanol, 210 g of acetonitrile, 3.6 g of polyethylene glycol-400, 37 g of fluorochloromethane, 15 g of sodium hydroxide and 60 g of water. Enable the reaction for 4 h at appropriate agitation and 50° C. Then, cool down to room temperature after reaction. Collect gas phase in air bag. Split the obtained solution into two layers. Separated colorless transparent organic layer at the top weighs 35 g. Analysis on obtained solution with gas chromatography shows 1,1,1,3,3,3-hexafluoroisopropanol conversion rate of 98%, and 65.12% of sevoflurane in 35 g of solution. The reaction has a yield of 65.15% with 1,1,1,3,3,3-hexafluoroisopropanol standard. Unreacted fluorochloromethane can be recovered for reuse.

Embodiment 18

Added in a three-neck flask of 250 ml are 30 g of 1,1,1,3,3,3-hexafluoroisopropanol, 30 g of N,N-dimethyl formamide, 16 g of bromofluoromethane and 12 g of tetrabutyle ammonium bromide. Put 10 g of sodium carbonate in 40 g of water to prepare sodium carbonate solution, to be slowly pipetted into the reaction process. Enable the reaction for 5 h at appropriate agitation speed. Allow the solution after reaction for distillation to obtain 20 g of pale yellow transparent solution. Analysis on distilled solution with gas chromatography shows bromofluoromethane conversion rate of 71%, and 65.86% of sevoflurane in 20 g of solution. The reaction has a yield of 64.94% with bromofluoromethane standard. Unreacted bromofluoromethane can be recovered for reuse.

The invention claimed is:

1. A preparation method of fluoromethyl 1,1,1,3,3,3-hexafluoroisopropyl ether comprising the single step of: reacting a liquid mixture consisting essentially of compounds as specified in a general formula (1), 1,1,1,3,3,3-hexafluoroisopropanol, an acid-binding agent, a solvent and a phase-transfer catalyst, $$CH_2FX \quad (1)$$

wherein: X is either Cl, Br or I; and
the solvent is selected from straight chain ether, cyclic ether, nitrile compound, N,N-dimethyl formamide, N,N-dimethyl acetamide, N-methylpyridine flavanone or dimethyl sulfoxide or their combination; wherein the yield is 46.69 or higher.

2. The preparation method of fluoromethyl 1,1,1,3,3,3-hexafluoroisopropyl ether according to claim 1, wherein said acid-binding agent is selected from an inorganic base or an organic base or their combination.

3. The preparation method of fluoromethyl 1,1,1,3,3,3-hexafluoroisopropyl ether according to claim 2, wherein said inorganic base is selected from metal oxide, metal hydroxide, metal carbonate or metal acid carbonate or their combination.

4. The preparation method of fluoromethyl 1,1,1,3,3,3-hexafluoroisopropyl ether according to claim 3, wherein said metal oxide is selected from alkali metal oxide or alkali soil metal oxide or their combination; said metal hydroxide is selected from alkali metal hydroxide or alkali soil metal hydroxide or their combination; said metal carbonate is selected from alkali metal carbonate or alkali soil metal carbonate or their combination; said metal acid carbonate is selected from alkali metal acid carbonate or alkali soil metal acid carbonate or their combination.

5. The preparation method of fluoromethyl 1,1,1,3,3,3-hexafluoroisopropyl ether according to claim 2, wherein said organic base is selected from amine or pyridine or their combination.

6. The preparation method of fluoromethyl 1,1,1,3,3,3-hexafluoroisopropyl ether according to claim 5, wherein said amine is selected from triethylamine, diethylamine, monoethanolamine, diethanolamine, 1,2-propylene diamine or tert-butylamine or their combination.

7. The preparation method of fluoromethyl 1,1,1,3,3,3-hexafluoroisopropyl ether according to claim 1, wherein said straight chain ether is selected from ether and/or dimethoxyethane; said cyclic ether is selected from dioxane and/or tetrahydrofuran; said nitrile compound is selected from acetonitrile and/or propionitrile.

8. The preparation method of fluoromethyl 1,1,1,3,3,3-hexafluoroisopropyl ether according to claim 1, wherein mass ratio of said solvent to 1,1,1,3,3,3-hexafluoroisopropanol is 50:1- 1:1.

9. The preparation method of fluoromethyl 1,1,1,3,3,3-hexafluoroisopropyl ether according to claim 8, wherein mass ratio of said solvent to 1,1,1,3,3,3-hexafluoroisopropanol is 7:1-1:1.

10. The preparation method of fluoromethyl 1,1,1,3,3,3-hexafluoroisopropyl ether according to claim 1, wherein said phase-transfer catalyst is selected from quaternary ammonium salt, phosphonium salt, oxidized sulfonium salt, pyridine salt or polyether compound or their combination.

11. The preparation method of fluoromethyl 1,1,1,3,3,3-hexafluoroisopropyl ether according to claim 10, wherein said quaternary ammonium salt is selected from tetrabutyl ammonium bromide, tetraethyl ammonium bromide or tetrabutyl ammonium hydrogen sulfate; said phosphonium salt is triphenylphosphine and polyether compound is polyethylene glycol.

12. The preparation method of fluoromethyl 1,1,1,3,3,3-hexafluoroisopropyl ether according to claim 1, wherein mol ratio of said phase-transfer catalyst to 1,1,1,3,3,3-hexafluoroisopropanol is 0.0001:1-1:1.

13. The preparation method of fluoromethyl 1,1,1,3,3,3-hexafluoroisopropyl ether according to claim 12, wherein mol ratio of said phase-transfer catalyst to 1,1,1,3,3,3-hexafluoroisopropanol is 0.01:1-0.2:1.

14. The preparation method of fluoromethyl 1,1,1,3,3,3-hexafluoroisopropyl ether according to claim 1, wherein reaction temperature is 0-300° C.

15. The preparation method of fluoromethyl 1,1,1,3,3,3-hexafluoroisopropyl ether according to claim 14, wherein said reaction temperature is 0-100° C.

16. The preparation method of fluoromethyl 1,1,1,3,3,3-hexafluoroisopropyl ether according to claim 1, wherein said mol ratio of acid-binding agent to 1,1,1,3,3,3-hexafluoroisopropanol is 2:1-1:2.

17. The preparation method of fluoromethyl 1,1,1,3,3,3-hexafluoroisopropyl ether according to claim 1, wherein mol ratio of said $CH_2FX$ to 1,1,1,3,3,3-hexafluoroisopropanol is 20:1-0.5:1.

18. The preparation method of fluoromethyl 1,1,1,3,3,3-hexafluoroisopropyl ether according to claim 17, wherein mol ratio of said $CH_2FX$ to 1,1,1,3,3,3-hexafluoroisopropanol is 3:1-0.8:1.

19. The preparation method of fluoromethyl 1,1,1,3,3,3-hexafluoroisopropyl ether according to claim 1, wherein reaction pressure is 0.1-2.0 MPa.

20. The preparation method of fluoromethyl 1,1,1,3,3,3-hexafluoroisopropyl ether according to claim 19, wherein reaction pressure is 0.1-0.5 MPa.

21. The preparation method of fluoromethyl 1,1,1,3,3,3-hexafluoroisopropyl ether according to claim 20, wherein reaction pressure is 0.1-0.3 MPa.

22. A preparation method of fluoromethyl 1,1,1,3,3,3-hexafluoroisopropyl ether, comprising the single step of: reacting a liquid mixture consisting essentially of $CH_2FBr$, 1,1,1,3,3,3-hexafluoroisopropanol, an acid-binding agent, a solvent and a phase-transfer catalyst; wherein the solvent selected from a straight chain ether, a cyclic ether, nitrile compound, N,N-dimethyl formamide, N,N-dimethyl acetamide, N-methylpyridine flavanone or dimethyl sulfoxide or their combination; wherein the yield is 46.69 or higher.

23. The preparation method of fluoromethyl 1,1,1,3,3,3-hexafluoroisopropyl ether according to claim 22, wherein reaction takes place at 0-300° C. and 0.1-2.0 MPa, with mass ratio of the solvent to 1,1,1,3,3,3-hexafluoroisopropanol at 50:1-1:1, mol ratio of the phase-transfer catalyst to 1,1,1,3,3,3-hexafluoroisopropanol at 0.0001:1-1:1, mol ratio of 1,1,1,3,3,3-hexafluoroisopropanol to the acid-binding agent at 2:1-1:2, and mol ratio of $CH_2FBr$ to 1,1,1,3,3,3-hexafluoroisopropanol at 20:1-0.5:1.

24. The preparation method of fluoromethyl 1,1,1,3,3,3-hexafluoroisopropyl ether according to claim 23, wherein reaction takes place at 0-100° C. and 0.1-0.3 MPa, with mass ratio of the solvent to 1,1,1,3,3,3-hexafluoroisopropanol at 7:1-1:1, mol ratio of the phase-transfer catalyst to 1,1,1,3,3,3-hexafluoroisopropanol at 0.01:1-0.2:1, and mol ratio of $CH_2FBr$ to 1,1,1,3,3,3-hexafluoroisopropanol at 3:1-0.8:1.

* * * * *